United States Patent [19]

Weeks

[11] Plant 5,130

[45] Nov. 1, 1983

[54] ROSE PLANT

[76] Inventor: O. L. Weeks, 926 W. Philadelphia, Ontario, Calif. 91761

[21] Appl. No.: 329,195

[22] Filed: Dec. 10, 1981

[51] Int. Cl.[3] ..... A01H 5/00

[52] U.S. Cl. ..... Plt./18

[58] Field of Search ..... Plt./18

*Primary Examiner*—Robert E. Bagwill

*Attorney, Agent, or Firm*—Vincent G. Gioia

[57] ABSTRACT

A new hybrid tea rose variety of Neyron rose coloring and strong rose fragrance.

1 Drawing Figure

The present invention relates to a new and distinct variety of rose plant of the hybrid tea rose class, named Sweet Surrender, which was originated by my crossing as seed parent an unnamed, unpatented rose of my creation and the rose known as "Tiffany" as pollen parent.

This new rose is a classic hybrid Tea with relatively clear Neyron rose coloring and the seed parent is lavender floribunda type. Foliage of the new variety is larger and heavier textured than the seed parent. The pollen parent (Tiffany) is more reddish pink with more yellow coloring at the petal base and significantly fewer petals. The new rose is flatter at maturity with ruffled petals and a pronounced heady real rose perfume.

Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminologyused in color description herein refers to plate numbers in the aforementioned color chart, e.g., "55C" is plate 55C of The Royal Horticultural Society Colour Chart.

Parentage: Seedling.

*Seed parent.*—Unnamed, unpatented seedling of my creation.

*Pollen parent.*—"Tiffany".

Class: Hybrid Tea.

The following observations are made of specimens grown outdoors in San Bernardino County, Calif., during the month of September.

1. FLOWER

Blooming habit: Recurrent.

A. Bud:

(1) *Size.*—Small, short.

(2) *Form.*—Pointed, ovoid.

(3) *Color.*—As sepals fall color is insignificant at first. As petals unfurl at point of attachment petals are pale greenish yellow quickly becoming Neyron rose 55C to 55B at petal undersurface to 55A at petal edge. The petal top surface maintains more 55A than petal undersurface.

(4) *Sepals.*—Extend beyond bud some with foliaceous appendages.

(5) *Peduncle.*—Length — Medium. Aspect — not straight, with some small prickles. Strength — erect, stiff. Color — near 138A.

B. Bloom:

(1) *Size.*—Average size when fully expanded — about 4 to 5 inches.

(2) *Borne.*—Singly and two to three together in clusters.

(3) *Form.*—High centered, ovoid at first, becoming flat, petals loosely roll outward, becoming ruffled at maturity.

(4) *Petalage.*—Number of petals under normal conditions — about 40 to 44.

(5) *Color.*—At $\frac{1}{3}$ to $\frac{1}{2}$ open stage, flowers are predominantly Neyron rose 55B with sporadic darkening at some petal edges. Upon aging color lightens somewhat tending to 55C. Petals ruffle at maturity.

C. Petals:

(1) *Texture.*—Moderate thin, soft.

(2) *Appearance.*—Inside satiny, outside velvety.

(3) *Form.*—Oval tending to rounded petal edges, some notching or scalloping.

(4) *Arrangement.*—Imbricated.

(5) *Petaloids in center.*—Few.

(6) *Persistence.*—Drop off cleanly.

(7) *Fragrance.*—Strong real rose fragrance.

(8) *Lasting quality.*—Good lasting quality.

2. REPRODUCTIVE ORGANS

A. Stamens, filaments and anthers:

(1) *Arrangement.*—Irregularly arranged around pistils, tucked in calyx, medium length, most with anthers.

(2) *Color.*—Yellow.

B. Pollen:

*Color.*—Yellow.

C. Styles: Uneven, short length, thin, bunched.

D. Stigmas:

*Color.*—Yellow.

E. Hips: None observed.

3. PLANT

A. Form: Upright.

B. Growth: Vigorous, free branching.

*Height attained.*—About $3\frac{1}{2}$ to 4 feet.

C. Foliage: Compound 3, 5 and 7 leaflets.

(1) *Size.*—Medium.
(2) *Quantity.*—Abundant.
(3) *Color.*—New foliage: Reddish green. Old foliage: Near 131A.
(4) *Shape.*—Oval, acuminate.
(5) *Texture.*—Upper side is waxy, leathery and under side is rough, veined.
(6) *Edge.*—Serrated.
(7) *Serration.*—Serrate, somewhat double.
(8) *Leaf stem.*—Color — near to 139B.
(9) *Stipules.*—Moderately long, medium wide, moderately long points.
(10) *Resistance to disease.*—Rust — Average. Mildew — Average.

D. Wood:
(1) *New wood.*—Color — near 139C. Bark — smooth.

(2) *Old wood.*—Color — near 139B. Bark — smooth.

E. Thorns:
(1) *Thorns.*—Quantity (main stalk) — ordinary. On laterals from stalk — ordinary. Form — flat, pointed. Length — short, downward curved. Color — tan to light green. Position — irregular.
(2) *Prickles.*—Few.

F. Winter hardiness: Average winter hardiness.

I claim:

1. A new and distinct variety of rose plant of the Hybrid Tea class, substantially as shown and described, characterized particularly by very fragrant Neyron rose flowers which open fully and are borne primarily singly or in small clusters on a vigorous plant with abundant foliage.

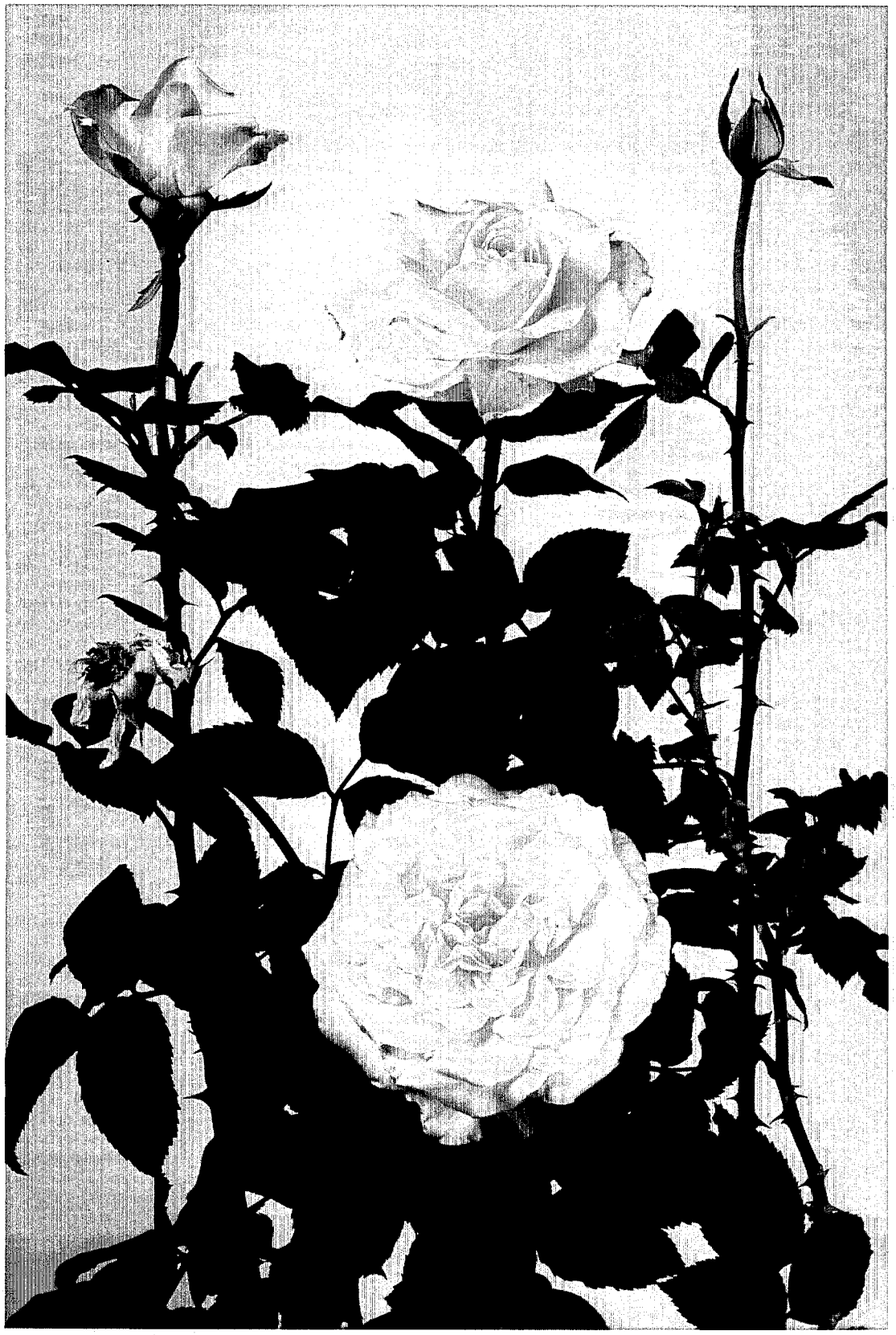

* * * * *